(12) United States Patent
Werner et al.

(10) Patent No.: US 7,695,677 B2
(45) Date of Patent: Apr. 13, 2010

(54) GLUCOSE ANALYSIS INSTRUMENT

(75) Inventors: Karl Werner, Wiesloch (DE); Peter Stephan, Mannheim (DE); Robert Lorenz, Worms (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 584 days.

(21) Appl. No.: 11/424,883

(22) Filed: Jun. 19, 2006

(65) Prior Publication Data

US 2006/0286620 A1 Dec. 21, 2006

(30) Foreign Application Priority Data

Jun. 18, 2005 (EP) .................................. 05013177

(51) Int. Cl.
*B01L 3/00* (2006.01)
(52) U.S. Cl. ...................... 422/61; 422/68.1; 435/14; 436/55; 436/95; 436/150
(58) Field of Classification Search .................. 422/61, 422/82.05, 98, 68.1; 435/14; 436/55, 95, 436/149, 150; 600/301, 316, 317, 322
See application file for complete search history.

(56) References Cited

U.S. PATENT DOCUMENTS

| | | | |
|---|---|---|---|
| 5,822,715 A * | 10/1998 | Worthington et al. | ......... 702/19 |
| 6,175,752 B1 * | 1/2001 | Say et al. | .................... 600/345 |
| 6,551,276 B1 * | 4/2003 | Mann et al. | ................. 604/131 |
| 6,572,542 B1 * | 6/2003 | Houben et al. | ............. 600/300 |
| 6,699,188 B2 * | 3/2004 | Wessel | ........................ 600/300 |
| 2002/0072858 A1 | 6/2002 | Cheng | |
| 2003/0125612 A1 | 7/2003 | Fox et al. | |
| 2003/0163789 A1 | 8/2003 | Blomquist | |
| 2003/0175806 A1 | 9/2003 | Rule et al. | |
| 2004/0030531 A1 * | 2/2004 | Miller et al. | ................ 702/182 |
| 2005/0113653 A1 | 5/2005 | Fox et al. | |

FOREIGN PATENT DOCUMENTS

WO  WO 01/74229  10/2001
WO  WO 2006037802 A2  4/2006

OTHER PUBLICATIONS

EP Search Report for Serial No. EP 06010874.3 mailed Oct. 30, 2006.

* cited by examiner

*Primary Examiner*—Jill Warden
*Assistant Examiner*—Dwayne K Handy
(74) *Attorney, Agent, or Firm*—Justin L. Sage; Roche Diagnostics Operations, Inc.

(57) ABSTRACT

Glucose analysis instrument for diabetics, comprising a measuring device for determining glucose concentration values, a displaying device for displaying glucose concentration values, a signaling device for generating a reminder signal, and a control and evaluation device that comprises a processor and a data memory and is used to determine reminder times at which the signaling device is actuated. Event data are stored in the data memory, the event data containing information on events occurring in the life of a user of the glucose analysis instrument and on the time of occurrence of such events. The reminder times are determined by means of a reminder time determination algorithm taking into consideration event data from at least one previous day.

19 Claims, 1 Drawing Sheet

GLUCOSE ANALYSIS INSTRUMENT

REFERENCE TO RELATED APPLICATIONS

The present application claims priority to and is based on European Patent Application No. 0513177.0, filed Jun. 18, 2005, which is hereby incorporated by reference in its entirety.

BACKGROUND OF THE INVENTION

The present invention relates to small, battery-operated, portable glucose analysis instruments such as used by diabetics as part of blood glucose self-monitoring. In particular, the present invention relates to a glucose analysis instrument for diabetics with a signaling device for generating a reminder signal.

Analytical instruments of this type are used to analyze a reaction that proceeds in an analysis element (also called "bio-sensor" or "test strip") after it contacts a sample liquid. The sample liquid is typically obtained by means of a skin prick, such as into a finger tip. Depending on the depth of the skin penetration, the sample liquid usually comprises a mixture of blood and interstitial fluid from the skin. Despite the fact that it is not pure blood that is being analyzed, it is customary to speak of "blood glucose analysis systems". The present invention relates in particular to such systems (so-called invasive systems that are customary for self-monitoring).

Glucose analysis instruments which additionally comprise a signaling device for generating a reminder signal are commercially available, for example under the trademark "ACCU-CHEK® GO". The signaling device of the ACCU-CHEK® GO glucose analysis instrument can be set for a many as three times of the day at which it reminds the user of a required blood glucose measurement, by means of an audio signal. The times of the day are selected by the user and entered into the instrument by means of keys.

Because glucose analysis instruments are typically taken along by diabetics at all times, a compact design is generally beneficial. A consequence of a compact design is that operating elements such as keys, buttons, displays, or similar aspects of the instrument can be provided only in very small form and generally few in number. Consequently, the inputting of times at which an audio signal is to be emitted as a reminder of a blood glucose measurement is difficult and inconvenient. This applies in particular to individuals whose manual abilities are reduced due to age or disease.

US 2003/0175806 A1 describes a blood glucose analysis instrument suitable for significantly more frequent determination of blood glucose concentration, as compared to customary instruments, in that the measurement is carried out at alternative measuring sites (Alternative Site Testing, or "AST"). The measuring method works without reagents, preferably in a non-invasive fashion. In this context, it is described as an option to carry out additional measurements by means of a conventional invasive ("finger-stick") analysis and to remind the user of the need to carry out a blood analysis measurement at a plurality of times during the day. According to an alternative described in this regard, the reminder time is not inputted into the instrument (like in the ACCU-CHEK® GO instrument), but rather it is determined taking into consideration the current glucose value, a nominal glucose value, and measured maximal and minimal values of the measured concentration. The instrument then stores a "case history" of concentration values that were measured which are then used by a processor of the instrument to determine the reminder times by means of mathematical prediction methods.

It is an object of the invention to provide an improved way by which users can be reminded of the need to carry out a blood glucose measurement at individually suitable times.

SUMMARY OF THE INVENTION

This object is achieved by a glucose analysis instrument for diabetics, comprising a measuring device for determining glucose concentration values, a displaying device for displaying glucose concentration values, a signaling device for generating a reminder signal, and a control and evaluation device that comprises a processor and a data memory and is used to determine reminder times at which the signaling device is actuated, the instrument being characterized in that event data of a user of the glucose analysis instrument are stored in the data memory, which event type data describe events belonging to a predefined type of event in the daily life of the user and the time of occurrence of such events, and in that the reminder times are determined with the processor by means of a reminder time determination algorithm taking into consideration event data from the same user and stored in the data memory over at least one day, but typically over a plurality of days to the extent enough data is available.

The event data stored in the data memory of the instrument according to the invention relate to previously selected (predefined) types of events in the life of the user. Predefined types of events can, in particular, be measurements of the glucose concentration, food intakes, resting times, and times of increased physical activity. However, in principle, other events that are characteristic of the daily routine of a user, for example start and end of the working hours, can be defined as event types and the corresponding event data can be stored.

In this context, two classes of event types must be distinguished, namely, (1) types of events that relate to a function of the glucose analysis instrument such that information related to these events is readily available in the analysis instrument ("internal events"), and (2) types of events that are characteristic of particularities in the daily routine of the user and do not relate to functions of the glucose analysis instrument such that information related to these events is not readily available (without additional means such as sensors) in the instrument ("external events"). The event data stored in the data memory of the instrument each contain information regarding the time at which an event corresponding to a predefined type of event occurs, and information regarding the particular event type.

The stored event times are typically the time of day at which the corresponding event occurs. With regard to events occurring over an extended period of time (such as a food intake or a resting period), the end or the middle of the time over which the event extends, can, for example, be stored as time of the event. Of course, the present invention is not limited to a particular form of detecting and storing the timing information which belongs to the event data. This timing information need not necessarily be stored as time of day. Rather, it can be favorable to measure and to store a time period, i.e. the duration between two events, in which case it is not necessary to measure and store the time of occurrence of the event as an absolute value (by time of day and date).

In one embodiment, the time period between the starts of two different event types can be detected and stored. For example, the event data may comprise the duration between a food intake and a glucose measurement. In this case, the determination of the reminder times (by the reminder time determination algorithm) is based on the duration between the occurrence of the two event types and there is no need to take into account the absolute times of day at which the events occurred. Such a possibility will be further explained below in the context of using an event time as floating reference point.

Typically, for the internal event type "measurement of a glucose concentration", the time at which an analysis is carried out is recorded. Obviously, the result of the analysis, i.e. the measured concentration, can additionally be stored. However, as will be explained below, it is desirable when executing the reminder time determination algorithm to use only the time of day at which the glucose analysis is carried out and not the result of the analysis.

The information concerning the occurrence of an external event type can be entered manually by the user by means of an input device of the instrument (e.g. by means of keys). However, the instrument can also comprise an event sensor that automatically recognizes the event and stores the corresponding event time. Relatively simple and cheap sensors are available, for example, for detecting certain physical activity, such as are used in step counters. They can be used with the present invention to automatically recognize both times of increased physical activity and resting times.

Compared to an instrument with manual input of the reminder times, the glucose analysis instrument according to the invention is characterized by its simplified operation and by the fact that the reminder times are adapted automatically and flexibly to the daily routine of the user. Although the method described in US 2003/0175806 A1 also allows an automatic generation of reminder signals, these signals do not adapt to the individual daily routine of the user. Rather, that disclosed method attempts to determine reminder times on the basis of analytical results. However this limited basis is unsuitable for the present invention because the resulting reminder time is then ultimately based on a prediction of the expected future development of the glucose concentration which is associated with great uncertainty.

In a glucose analysis instrument according to the present invention, there is no need for the user to enter any times of day into the instrument. The evaluation device independently utilizes data of the previous behavior of the user to determine the times at which the signaling device generates a reminder signal.

In determining reminder times, the control and evaluation device of the instrument independently adapts to the individual daily routine and behavior of a user. In one embodiment, the control and evaluation device independently adapts to a change in the daily rhythm, which may for example be caused by seasonal changes. The control and evaluation device of an instrument according to the present invention therefore is a self-training alarm system reminding the user automatically to perform a certain action, such as measuring blood glucose concentration, as well as other important actions for the treatment of diabetes. The reminder times at which the signaling device is actuated can be determined, for example, by applying a pattern recognition method to the stored event data.

In order to determine the reminder times, the control and evaluation device analyzes at least a part of the stored event data, the event data used in the analysis being distributed over a plurality of days. In one embodiment, the control and evaluation device accumulates event data in the form of daily routine profile data for between about 5 days and about 12 days, and uses at least a part of these total data in the reminder time determination algorithm to determine a reminder time. In other embodiments, the event data is accumulated over the course of between about 4 days and about 14 days. The length of accumulation can, as will be explained below, affect the degree of flexibility of the control and evaluation device in determining reminder times.

In one embodiment, the reminder times can be determined automatically. In addition, flexible adaptation to the lifestyle rhythm of the respective user is achievable. For example, relatively young and independent diabetics often have a very irregular daily routine—due to the work and personal planning differing from one day to the next. As part of the present invention it was found that in these cases a reminder time determination that is oriented on medical measurement results does not provide satisfactory results. The invention allows for flexible combination of various event data in the reminder time determination algorithm and thus for adaptation of the reminder times to the individual lifestyle rhythm of the user.

In order to optimize this flexibility, the control and evaluation device in one embodiment uses different reminder time determination algorithms for working days versus non-working days. In other embodiments, the control and evaluation device uses an event time as a non-static reference point (floating reference point) in the reminder time determination algorithm. For example, food intakes are a particularly well-suited illustration of this. It can be helpful to determine over the course of several days, using the reminder time determination algorithm, the period of time between a food intake (for example, lunch) and the subsequent measurement of the glucose concentration and to generate a reminder signal at a point in time that is related to the corresponding food intake (for example, lunch) on the respective day. In this simple example, the reminder signal from the signaling device may be generated at a certain period of time after the lunch, with the period of time corresponding to the mean of the periods of time between the blood glucose measurements and the corresponding lunches on the preceding days. Obviously, the mean is only a simple example. In more comprehensive embodiments, mathematical procedures are utilized that provide for more flexible adaptation while taking into consideration multiple parameters, e.g. the types of events and particular event data. The simplified example illustrates, however, that the use of a floating reference point has particular utility with regard to the flexible adaptation to the habits of the user since the user is reminded of carrying out a glucose measurement not at a more or less fixed time of day, but rather at a point in time that corresponds to his personal daily routine. Here, the time period between the event time used as floating reference point and the reminder time can have any value, including zero (in which case the reminder signal is generated simultaneously with the occurrence of the event which is used as floating reference point).

Thus the present invention permits the determination of reminder times that can be individually adapted to the daily rhythm of a user and in addition depend on events that are relevant to the time profile of the blood glucose concentration, for example food intakes, insulin administrations or physical activity.

The determination of reminder times as part of the present invention is not limited to the timing of required glucose analyses. Rather, in other embodiments, reminder times for other actions can also be determined according to the invention, such as for insulin administrations and/or food intakes. In this regard, it can be helpful to generate different reminder signals for the different user actions being reminded with the signaling device. Generally, acoustic signals are one means of signaling, but it is also feasible to use visual reminder signals (for example indicia on a display) or haptic reminder signals (e.g. vibrations).

For example, the control and evaluation device can determine a first class of reminder times at which the signaling device generates a first type of reminder signal as a reminder of a required blood glucose measurement, and, in addition, determines a second class of reminder times at which the signaling device generates a second type of reminder signal as a reminder of insulin injections, food intakes and/or sports activities.

DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF EMBODIMENTS OF THE PRESENT INVENTION

The following description of the preferred embodiment is merely exemplary in nature and is in no way intended to limit the invention or its application or uses.

Figure 1:
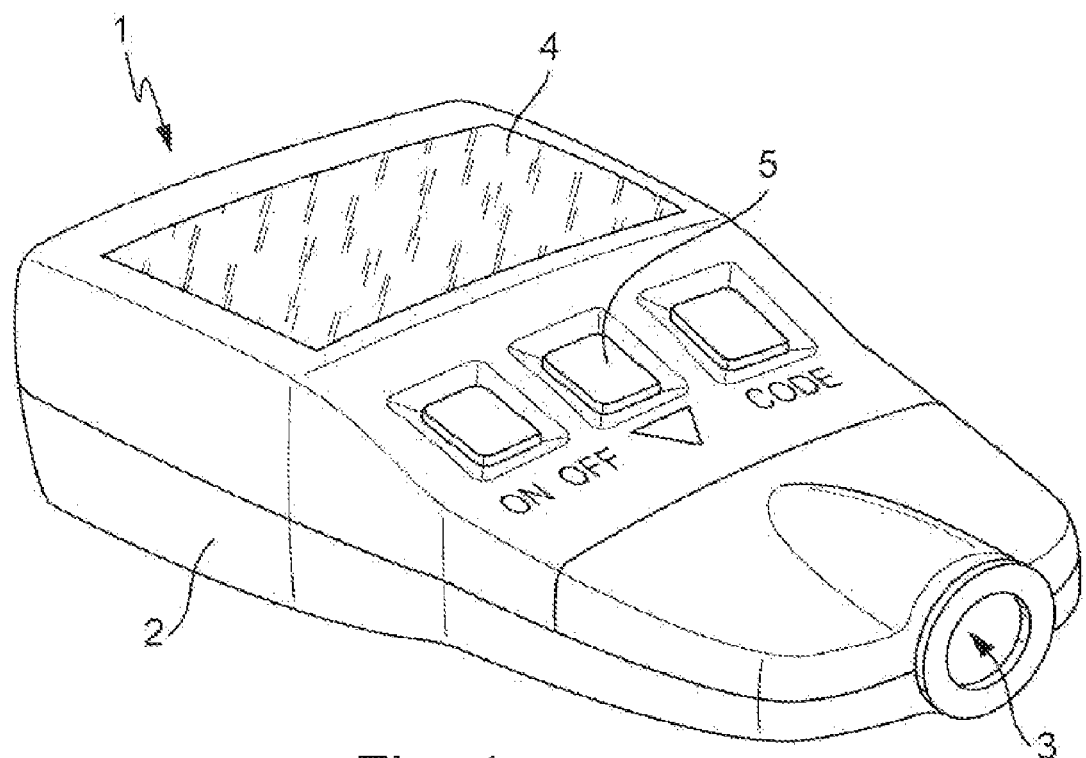
FIG. 1 shows a perspective view of a glucose analysis instrument.

The external appearance of the glucose analysis instrument 1 shown in FIG. 1 corresponds to that of known instruments. A displaying device 4 in the form of a display serves to show measuring values and any other information desired to be displayed. Operating elements 5 in the form of keys or buttons are provided for actuating the analytical instrument 1 and/or for special functions. In one embodiment, a lancet (not shown) is provided inside the instrument and can be used to generate a prick wound in a body part, for example a finger held against an opening 3 of the housing 2. The instrument 1 takes up blood emerging from the prick wound and uses a measuring device (see FIG. 2) to determine a blood glucose concentration value. In other embodiments, instrument 1 comprises opening 3 configured to receive and electrically connect to an analysis element (not shown), and a separate lancing device (not shown) is employed by the user to draw a blood sample from a site on the user's body, the sample being then introduced to the analysis element for analysis by the instrument.

The glucose analysis instrument 1 can be equipped with an independent power source (not shown), for example commercial batteries, that supplies current to the individual components. The corresponding components of the glucose analysis instrument 1 are known and thus do not need to be illustrated in more detail.

Figure 2:
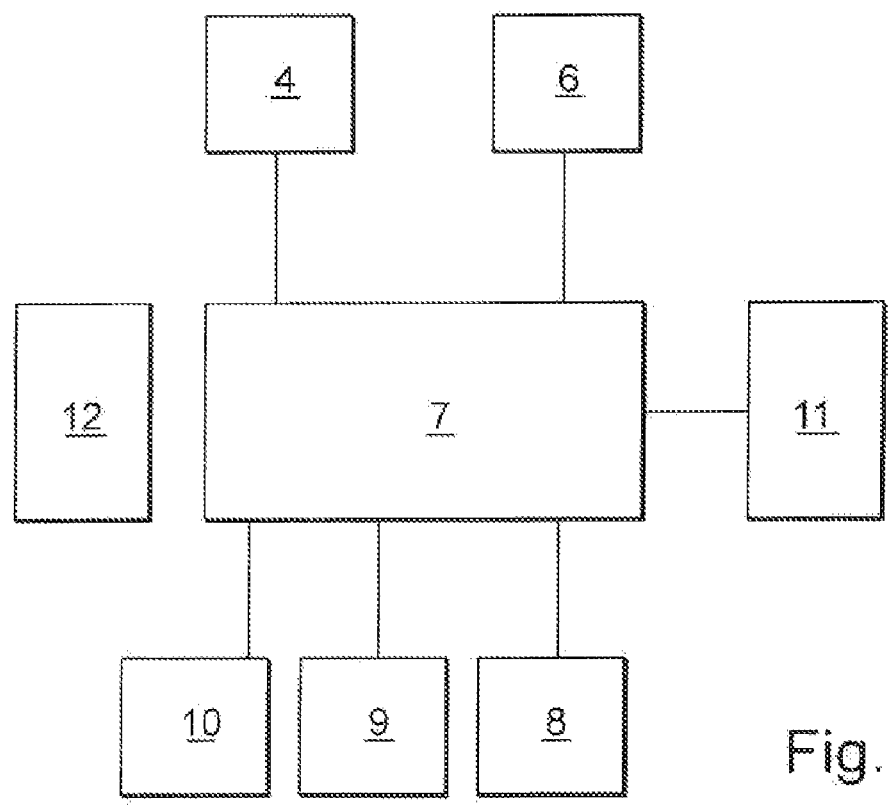
FIG. 2 shows a block diagram of the glucose analysis instrument shown in FIG. 1.

FIG. 2 shows a block diagram of the components of a glucose analysis instrument 1, in the form of a schematic representation. The glucose content of a blood sample is determined by means of a measuring device 6 that is connected to a control and evaluation device 7. Here, the totality of all components used by the analysis instrument to measure (usually on an analysis element) a physical parameter that is characteristic of the analysis and to determine therefrom the desired glucose concentration is designated "measuring device". A more detailed description is not required in this context, since numerous measuring devices of this type and various methodologies employed by them are known and the exact type of the analytical procedure is not important for the purposes of this disclosure.

The control and evaluation device 7 typically contains a microprocessor. Glucose concentration values that have been determined by the measuring device 6 are stored in a non-volatile data memory 8 and can be displayed to a user by means of the display 4.

Moreover, the glucose analysis instrument 1 is provided with an internal time measuring device 9 that can, for example, utilize a clock generator that may be provided with the control and evaluation device 7. A signaling device 10 serves to remind a user of the need to carry out a blood glucose measurement (or to conduct some other action), for example by means of an acoustic signal.

In one embodiment, in the data memory 8 are stored the event data, such as glucose concentration measuring times (the times at which glucose concentration values were measured), as well as the correspondingly measured glucose concentration values. The control and evaluation device 7 is configured to use the stored event data to determine reminder times at which the signaling device 10 is actuated by the control and evaluation device 7. These reminder times are determined by the control and evaluation device 7 using a method (algorithm) that is illustrated hereafter. Initially a very simple method, in which only the event data of glucose analyses are taken into consideration, will be described.

According to one embodiment of the present invention, the first time the glucose analysis instrument 1 is ever used, no event data, e.g. times at which blood glucose measurements were performed, are available. Event data from the first day of use of the instrument is collected an accumulated, and the control and evaluation device 7 commences determining reminder times only on the second day, accessing the stored event data, such as the times at which blood glucose measurements were performed on the first day. For example, typically the stored event data of the first day of operation are used as reminder times on the second day of operation. As a result, the signaling device 10 is actuated by the control and evaluation device 7 on the second day at generally the same time of day at which events, e.g. blood glucose measurements, were carried out on the first day of operation.

For the third day and all subsequent days of operation, the reminder times should be re-calculated. For example, the event times that are within a pre-set time interval from the most recently used reminder times can be taken into consideration to adjust the current day's reminder times. The new reminder time is calculated a the mean of these event times.

The magnitude of this pre-set time interval should be selected such that, for example, event times of the first glucose measurement of a particular day are not taken into consideration in the calculation of the reminder time for the second measurement of the same day. Accordingly, the time interval should be small enough that only event times of the $n^{th}$ measurements of previous days are contained in the time interval for the calculation of the reminder time of the $n^{th}$ measurement of the current day. The pre-set time interval preferably comprises approximately one to two hours.

With regard to the calculation of reminder times, it is possible to use only event data of a limited period of time of, for example, two weeks, such that an adaptation to a changed daily rhythm occurs over a foreseeable period of time. The shorter this period of time, the more immediately the reminder times will reflect changed lifestyle habits. However, this period of time should not be too short to prevent measurements which are for special reasons carried out at uncommon times to have an undesirably large influence on the calculation of the reminder times. In one embodiment, the event data of the preceding 4 to 14 days is used in the calculation of the reminder times.

In other embodiments the control and evaluation device provides the user with the option to delete stored event data or to enter such data into the instrument for the first day of operation. For this purpose, the displaying device 4 can be used to display an operating menu from which suitable functions are selected by means of the operating keys 5.

As mentioned, the preceding description concerned a relatively simple reminder time determination algorithm and some variants thereof. However, considering the processor and data storage capability which is available today even in small, battery-operated instruments, much more sophisticated algorithms can be used. A detailed discussion is not feasible due to the large number of possible variants. Moreover, it is not necessary since the mathematical procedures are known and largely available as commercial program components. The advantages that are associated with the present invention and its possible developments, as illustrated above, can be achieved with different variants of such commercially available algorithms.

As was illustrated above, the invention is not limited to measurements of the glucose concentration as the type of event. Rather, in other embodiments it is possible to use event data of other, in particular of external, types of events. These can be transmitted to the control and evaluation device 7 either manually by means of an input device 11 or automatically by means of an event sensor 12.

Repeat measurements that were carried out, for example, to verify measured values of particularly high or low glucose concentration value that lie outside typical measured values, should not typically be used in the determination of reminder times. In this regard, in one embodiment the control and evaluation device is configured to compare current glucose concentration values to historical measured values and, on the basis of this comparison, to independently remind the user after a pre-set time of, for example, 20 minutes of the need for a repeat measurement.

Improved convenience for the user can be provided by using a different reminder time determination algorithm for working days versus non-working days. Most people have a different daily rhythm on working days as compared to non-working days (vacation days, holidays, and weekend days). One possible way to switch the reminder time determination algorithm between working and non-working days is to have the user instruct the instrument 1 by means of a key stroke whether or not the current day is a non-working day. In a similar manner, another reminder time determination algorithm can be provided also for other special situations of life, such as times of illness, when daily rhythms are generally also different from both working days and non-working days.

In one embodiment, the control and evaluation device actuates the signaling device 10 also to remind a user to perform other actions, e.g. a basal injection (an insulin injection to meet the user's basic need). Reminder times for other actions such as basal injections can be determined using yet another reminder time determination algorithm. In such embodiments, it is typically necessary to instruct the instrument of the time the action (e.g. basal injection) takes place. In the simplest case, this can be done by a key stroke such that the time of the key stroke is stored in the data memory 8 as the event time of the action. In other embodiments, the signaling device 10 generates a different signal for a reminder of a blood glucose measurement as compared to a reminder for other actions, such as a basal injection. Reminder signals that are easily distinguished by the human ear can be generated, for example, by different sound frequencies or sequences of sounds.

The control and evaluation device 7 can also be used to automatically remind the user of corrective insulin administrations, food intakes or physical activities taking into consideration event data (e.g. concerning insulin administrations, food intakes, and physical activities) and possibly additionally analyzing measured values of the blood glucose concentration that are stored in the data memory 8.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. Glucose analysis instrument for diabetics, comprising:
   a measuring device for determining glucose concentration values,
   a displaying device for displaying the glucose concentration values,
   a signaling device for generating a reminder signal, and
   a control and evaluation device which comprises a processor and a data memory and is used to determine reminder times at which the signaling device is actuated,
   wherein event data are stored in the data memory, said event data comprising information on one or more events occurring in the life of a user of the instrument, said events belonging to at least one predefined type of events, said type of events including food intake, said information including the type of the event and the time the event occurs; and
   wherein the reminder times are determined by means of a reminder time determination algorithm executed with the processor using event data including the type of event and the time the event occurs from a plurality of days; and wherein information relating to a time an event occurs is used as a floating reference point in the reminder time determination algorithm for calculating the reminder time by adding a time period to the floating reference point.

2. Glucose analysis instrument according to claim 1, wherein the event data are accumulated in the data memory for between about 5 previous days and about 12 previous days during the use of the instrument.

3. Glucose analysis instrument according to claim 1, wherein the event data are accumulated in the data memory for between about 4 previous days and about 14 previous days during the use of the instrument.

4. Glucose analysis instrument according claim 1, wherein the type of the event comprises an internal event corresponding to use of the glucose analysis instrument.

5. Glucose analysis instrument according to claim 4, wherein the use of the glucose analysis instrument comprises glucose concentration measurements.

6. Glucose analyses instrument according to claim 5, wherein the reminder time determination algorithm comprises a functional step that prevents actuation of the signaling device at a reminder time if a glucose concentration measurement was carried out in a pre-set waiting period of at least 20 minutes prior to the reminder time.

7. Glucose analysis instrument according to claim 1, wherein the type of the event comprises an external event corresponding to actions or activities of a user conducted other than by using the glucose analysis instrument.

8. Glucose analysis instrument according to claim 7, wherein the external event comprises one or more of the group consisting of food intakes of the user, resting periods of the user, insulin administrations, basal injections, and periods of physical activity of the user.

9. Glucose analysis instrument according to claim 7, wherein information about the occurrence of the external event is generated automatically by means of an event sensor included with the glucose analysis instrument.

10. Glucose analysis instrument according to claim 7, wherein information about the occurrence of the external event is entered manually by means of an input device included with the glucose analysis instrument.

11. Glucose analysis instrument according to claim 1, wherein the reminder time determination algorithm comprises a pattern recognition method.

12. Glucose analysis instrument according to claim 1, wherein the reminder times for working days and for non-working days are determined by means of different reminder time determination algorithms.

13. Glucose analysis instrument according to claim 1, wherein the data memory is non-volatile.

14. Glucose analysis instrument according to claim 1, wherein the signaling device generates acoustic reminder signals.

15. Glucose analysis instrument according to claim 1, wherein the control and evaluation device determines a first class of reminder times at which the signaling device generates a first type of reminder signal as a reminder of a blood glucose concentration measurement, and wherein the control and evaluation device determines a second class of reminder times at which the signaling device generates a second type of reminder signal as a reminder of an insulin injection.

16. A method for reminding a diabetic to conduct a certain action, comprising the steps of:
 (a) providing a glucose analysis instrument comprising:
  a measuring device for determining glucose concentration values,
  a displaying device for displaying the glucose concentration values,
  a signaling device for generating a reminder signal, and
  a control and evaluation device comprising a processor including a reminder time determination algorithm and comprising a data memory;
 (b) storing event data in the data memory, said event data comprising information on one or more events, said events belonging to at least one predefined type of events, said type of events including food intake, said information including the type of the event and the time the event occurs, said event data being from a plurality of days;
 (c) determining, using the reminder time determination algorithm, reminder times at which the control and evaluation device is to actuate the signaling device, wherein the reminder time determination algorithm is executed using event data including the type of event and the time the event occurs, and wherein information relating to a time an event occurs is used as a floating reference point in the reminder time determination algorithm for calculating the reminder time by adding a time period to the floating reference point.

17. The method of claim 16, wherein the action to be reminded comprises a glucose concentration measurement or an insulin injection.

18. The method of claim 16, wherein the one or more events comprise one or more from the group consisting of a glucose concentration measurement, an insulin injection, food intake by a user of the glucose analysis instrument, a resting period of the user, and a period of physical activity of the user.

19. The method of claim 16, comprising the steps of determining a first class of reminder times at which the signaling device generates a first type of reminder signal as a reminder of a blood glucose concentration measurement, and determining a second class of reminder times at which the signaling device generates a second type of reminder signal as a reminder of an insulin injection, wherein the processor of the control and evaluation device includes different reminder time determination algorithms for each of the first and second class of reminder times.

* * * * *